(12) United States Patent
Shen et al.

(10) Patent No.: US 11,241,679 B2
(45) Date of Patent: Feb. 8, 2022

(54) ORDERED MACROPOROUS METAL-ORGANIC FRAMEWORK SINGLE CRYSTALS AND PREPARATION METHOD THEREOF

(71) Applicant: SOUTH CHINA UNIVERSITY OF TECHNOLOGY, Guangdong (CN)

(72) Inventors: Kui Shen, Guangdong (CN); Yingwei Li, Guangdong (CN); Yonghai Cao, Guangdong (CN); Junying Chen, Guangdong (CN)

(73) Assignee: SOUTH CHINA UNIVERSITY OF TECHNOLOGY, Guangdong (CN)

( * ) Notice: Subject to any disclaimer, the term of this patent is extended or adjusted under 35 U.S.C. 154(b) by 569 days.

(21) Appl. No.: 16/330,103

(22) PCT Filed: Nov. 27, 2017

(86) PCT No.: PCT/CN2017/113129
§ 371 (c)(1),
(2) Date: Mar. 4, 2019

(87) PCT Pub. No.: WO2019/052014
PCT Pub. Date: Mar. 21, 2019

(65) Prior Publication Data
US 2021/0213436 A1    Jul. 15, 2021

(30) Foreign Application Priority Data
Sep. 13, 2017 (CN) .......................... 201710819873.9

(51) Int. Cl.
| | | |
|---|---|---|
| *B01J 31/16* | (2006.01) | |
| *B01J 37/00* | (2006.01) | |
| *B01J 37/02* | (2006.01) | |
| *B01J 37/06* | (2006.01) | |
| *C07D 233/58* | (2006.01) | |

(52) U.S. Cl.
CPC ....... *B01J 31/1691* (2013.01); *B01J 37/0018* (2013.01); *B01J 37/0203* (2013.01); *B01J 37/0205* (2013.01); *B01J 37/0236* (2013.01); *B01J 37/06* (2013.01); *C07D 233/58* (2013.01)

(58) Field of Classification Search
None
See application file for complete search history.

(56) References Cited

FOREIGN PATENT DOCUMENTS

| CN | 103159186 | 6/2013 |
| CN | 105220012 | 1/2016 |

OTHER PUBLICATIONS

Zhang et al."Hollow Zeolitic Imidazolate Framework Nanospheres as Highly Efficient Cooperative Catalysts for [3+3] Cycloaddition Reactions" Journal of the American Chemical Society, 2014, vol. 136, No. 40, pp. 13963-13966.*

Banerjee et al., "High-Throughput Synthesis of Zeolitic Imidazolate Frameworks and Application to CO2 Capture", Science, Feb. 15, 2008, pp. 939-943.

Li et al., "Selective gas adsorption and separation in metal-organic frameworks", Chemical Society Reviews, Mar. 26, 2009, cover page and pp. 1477-1504.

Furukawa et al., "Structuring of metal-organic frameworks at the mesoscopic/macroscopic scale", Chem Soc Rev, May 9, 2014, pp. 5700-5734.

Xuan et al., "Mesoporous metal-organic framework materials", Chem Soc Rev, Oct. 18, 2011, pp. 1677-1695.

Eddaoudi et al., "Systematic Design of Pore Size and Functionality in Isoreticular MOFs and Their Application in Methane Storage", Science, Jan. 18, 2002, pp. 469-472.

Deng et al., "Large-Pore Apertures in a Series of Metal-Organic Frameworks", Science, May 25, 2012, pp. 1018-1023.

Zhao et al., "Metal-Organic Framework Nanospheres with Well-Ordered Mesopores Synthesized in an Ionic Liquid/CO2/Surfactant System", Angewandte Chemie, Dec. 9, 2010, pp. 636-639.

Zhang et al., Mesoporous Metal-Organic Frameworks with Size-, Shape-, and Space-Distribution-Controlled Pore Structure, Advanced Materials, Mar. 31, 2015, pp. 2923-2929.

Han et al., "Simple and Efficient Regeneration of MOF-5 and HKUST-1 via Acid-Base Treatment", Crystal Growth & Design, Oct. 7, 2015, pp. 5568-5572.

El-Hankari et al., "Surface etching of HKUST-1 promoted via supramolecular interactions for chromatography", Journal of Materials Chemistry A, Jul. 2, 2014, pp. 13479-13485.

Taylor et al., "Defect Control To Enhance Proton Conductivity in a Metal-Organic Framework", Chemistry of Materials, Mar. 20, 2015, pp. 2286-2289.

Wu et al., "Unusual and Highly Tunable Missing-Linker Defects in Zirconium Metal-Organic Framework UiO-66 and Their Important Effects on Gas Adsorption", Journal of the American Chemical Society, Jun. 28, 2013, pp. 10525-10532.

"International Search Report (Form PCT/ISA/210)", dated May 30, 2018, pp. 1-4.

* cited by examiner

*Primary Examiner* — Joseph R Kosack

(57) ABSTRACT

An ordered macroporous metal-organic framework single crystals and a preparation method therefor. In the method, a three-dimensional structure constructed by polymer microspheres is used as a template; 2-methylimidazole and zinc nitrate, precursors of MOFs, are firstly deposited in the three-dimensional template; the three-dimensional template containing the precursors is soaked in a mixed solution of ammonia water and methanol subsequently, and the three-dimensional template is taken out after crystallization; the three-dimensional template is soaked in an organic solvent to remove the macromolecular three-dimensional template, and the ordered macroporous MOF single crystals is obtained through centrifugal separation. The ordered macroporous MOF single crystals have a basic framework of zeolitic imidazolate framework-8, and structurally include highly-ordered macro-pores whose pore size may be controlled to be between 50 and 2000 nm based on a size of the used template.

18 Claims, 4 Drawing Sheets

ORDERED MACROPOROUS METAL-ORGANIC FRAMEWORK SINGLE CRYSTALS AND PREPARATION METHOD THEREOF

CROSS-REFERENCE TO RELATED APPLICATION

This application is a 371 application of International PCT application serial no. PCT/CN2017/113129, filed on Nov. 27, 2017, which claims the priority benefit of Chinese application no. 201710819873.9, filed on Sep. 13, 2017. The entirety of each of the above-mentioned patent applications is hereby incorporated by reference herein and made a part of this specification.

BACKGROUND

Technical Field

The present invention relates to the technical field of metal-organic frameworks (MOFs) preparation, and in particular, relates to ordered macroporous MOF single crystals and a preparation method thereof.

Description of Related Art

Based on the theory of coordination polymers, metal-organic frameworks (MOFs) are zeolite-like materials which are constructed from multi-dentate organic ligands containing oxygen and nitrogen linked to metal atoms or metal atom clusters by coordination bonds, and are formed with a periodic network structure by self-assembling. The MOFs have many excellent properties that are not found in other conventional materials (for example, high specific surface and porosity, rich and varied topologies, and mild and simple synthesis conditions and the like). Therefore, the MOFs have great potential applications in many fields such as hydrogen storage, adsorption, drug production, catalysis and the like (R. Banerjee, A. Phan, B. Wang, C. Knobler, H. Furukawa, M. O'Keeffe, O. M. Yaghi, *Science* 2008, 319, 939-943; J.-R. Li, R. J. Kuppler, H.-C. Zhou, *Chem. Soc. Rev.* 2009, 38, 1477-1504.). However, despite a large variety of MOFs and excellent properties in many applications, most of the reported MOFs have pore sizes that are concentrated in a micropore range (less than 2 nm), and the polymer diffusion resistance in the micropores severely affects application of the MOFs in many fields. In addition, narrow pore channels also restrict its further functionalization efficiency of MOFs (S. Furukawa, J. Reboul, S. Diring, K. Sumida, S. Kitagawa, *Chem. Soc. Rev.* 2014, 43, 5700-5734; W. Xuan, C. Zhu, Y. Liu, Y. Cui, *Chem. Soc. Rev.* 2012, 41, 1677-1695). Therefore, it is a great challenge for material workers to prepare a novel hierarchical-structured MOFs suitable for macromolecular reactions such that these MOFs exhibit superior properties over other single microporous-structured MOFs in terms of diffusion, mass transfer and the like. This is also a high requirement imposed on the field of MOFs with the development of the society.

At present, studies on the hierarchical-structured MOFs are still at the initial stage. Therefore, there is no universal synthesis mechanism and preparation method. Firstly, for preparation of MOFs with a mesoporous structure, many research groups use long-chain ligands instead of short-chain ligands for crystallization during the synthesis. Although a series of hierarchical-structured MOFs may be obtained with this method, and the pore sizes of the MOFs may also be effectively controlled according to the lengths of the ligands, after the short-chain ligands are replaced by the long-chain ligands in the MOFs, periodicity of the framework is hard to maintain or pore channel windows with a great diffusion resistance may be easily formed. Secondly, after guest molecules are removed from the formed hierarchical porous MOFs, the framework thereof may be easily collapsed (M. Eddaoudi, J. Kim, N. Rosi, D. Vodak, J. Wachter, M. O'Keeffe, O. M. Yaghi, *Science* 2002, 295, 469-472; H. Deng, S. Grunder, K. E. Cordova, C. Valente, H. Furukawa, M. Hmadeh, F. Gandara, A. C. Whalley, Z. Liu, S. Asahina, *Science* 2012, 336, 1018-1023). To solve this problem, the researchers have also developed many other methods, for example, a template method (Y. Zhao, J. Zhang, B. Han, J. Song, J. Li, Q. Wang, *Angew. Chem. Int. Ed.* 2011, 50, 636-639; W. Zhang, Y. Liu, G. Lu, Y. Wang, S. Li, C. Cui, J. Wu, Z. Xu, D. Tian, W. Huang, *Adv. Mater.* 2015, 27, 2923-2929), an etching method (S. Han, M. S. Lah, *Cryst. Growth Des.* 2015, 15, 5568-5572; S. El-Hankari, J. Huo, A. Ahmed, H. Zhang, D. Bradshaw, *J. Mater. Chem. A* 2014, 2, 13479-13485), a defect induction method (J. M. Taylor, S. Dekura, R. Ikeda, H. Kitagawa, *Chem. Mater.* 2015, 27, 2286-2289; H. Wu, Y. S. Chua, V. Krungleviciute, M. Tyagi, P. Chen, T. Yildirim, W. Zhou, *J. Am. Chem. Soc.* 2013, 135, 10525-10532), and the like. However, until now, all the reported methods have failed to produce MOFs with ordered/macro pores, and the pore size is generally limited to 10 nm or less. Meanwhile, it is difficult to obtain MOFs with a single crystal structure. Apparently, for the sake of improving use efficiency of the conventional MOFs in many applications, the above issue needs to be addressed, and a new pathway for preparing ordered macroporous MOFs single crystals needs to be proposed.

SUMMARY

The present invention is intended to overcome the defects of conventional microporous MOFs, and provide ordered macroporous MOF single crystals with a three-dimensional structure by using polymer microspheres as a template, and a preparation method thereof. The ordered macroporous MOF single crystals prepared by using the preparation method is composed of 2-methylimidazole and zinc ions, and thus has a basic framework of zeolitic imidazolate framework-8 (ZF-8) and adjustable macro pores. The ordered macroporous MOF single crystals have high purity, complete structure and strong mechanical strength, and achieve good stability and high catalytic efficiency.

The present invention is practiced by using the following technical solution:

A preparation method of ordered macroporous metal-organic framework single crystals is provided. The method comprises the following steps:

(1) dispersing polymer microspheres into a solvent, and preparing, through simple filtering and high-speed centrifugation, a three-dimensional template having periodic pore channels that is constructed by the polymer microspheres;

(2) soaking the three-dimensional template obtained in step (1) into a solution of 2-methylimidazole and zinc nitrate, standing still for 0 to 12 hours followed by vacuum treating for 0 to 2 hours, and then taking out the three-dimensional template and drying to obtain a three-dimensional template containing 2-methylimidazole and zinc nitrate;

(3) adding the three-dimensional template containing 2-methylimidazole and zinc nitrate obtained in step (2) into a mixed solution of ammonia water and methanol, vacuum treating for 0 to 2 hours followed by standing still for 1 to 48 hours, and then filtering, washing and drying;

(4) adding a solid obtained after drying in step (3) into an organic solvent for soaking, and then washing, and obtaining the ordered macroporous metal-organic framework single crystals through centrifugal separation.

Preferably, the polymer microspheres in step (1) are polystyrene microspheres, polymethylmethacrylate microspheres, chitosan microspheres or polylactic acid microspheres having a uniform size.

Preferably, the solvent in step (1) is one or a mixture of methanol, ethanol, acetone, deionized water, dichloromethane and ethyl acetate.

Preferably, an amount of the three-dimensional template in step (2) is 5 g.

Preferably, a molar ratio of 2-methylimidazole to zinc nitrate in step (2) is (0.5-5):1.

Preferably, a solvent of the solution in step (2) is one or a mixture of methanol, ethanol, acetone, deionized water, dichloromethane and ethyl acetate.

Preferably, a mass ratio of 2-methylimidazole to the solvent in step (2) is 0.001 to 0.5 g/ml.

Preferably, the drying in step (2) and step (3) is common drying.

Preferably, a volume ratio of methanol to the ammonia water in step (3) is (0-10):1.

Preferably, the organic solvent in step (4) is one or a mixture of N,N-dimethylformamide (DMF), toluene, tetrahydrofuran (THF), dichloromethane and chloroform.

Preferably, the soaking in step (4) lasts for 1 to 48 hours.

The ordered macroporous metal-organic framework single crystals prepared by using the above preparation method have the basic framework of zeolitic imidazolate framework-8 (ZIF-8), and structurally include ordered macro pores whose pore size may be controlled to be between 50 and 2000 nm based on a size of the used template.

As compared with the prior art, the present invention has the following advantages:

(1) The single crystals prepared according to the present invention is the first ordered macroporous single crystals MOF in the field of MOFs. The pore size of the ordered macroporous single crystals MOF may be controlled to be between 50 and 1000 nm based on the size of the used template. However, current literatures and patents have reported that the pore size of the MOF is generally 10 nm or less, which is far less than the pore size of the MOF prepared according to the present invention.

(2) The preparation process according to the present invention is simple, safe and controllable, and consumes less time and energy. The most important point is that the prepared ordered macroporous MOF single crystals has a high catalytic efficiency for macromolecular conversion, and achieves a catalytic activity that is much higher than that of a microporous ZIF-8 catalyst prepared by conventional methods when being used in a Knoevenagel reaction between benzaldehyde and ethanedinitrile

DESCRIPTION OF THE EMBODIMENTS

Figure 1:
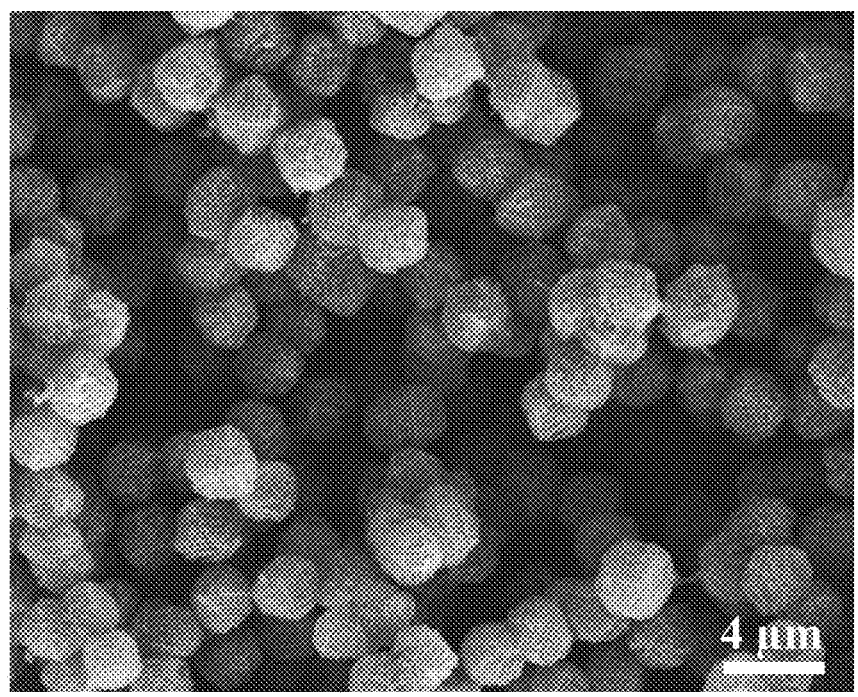
FIG. 1 is a scanning electron microscope image of ordered macroporous MOF single crystals prepared in Example 4 of the present invention.

Specific implementation of the present invention is further described in detail with reference to the accompanying drawings and specific examples. However, the implementation of the present invention is not limited hereto.

Example 1

500 ml of deionized water, 65 ml of styrene and 2.5 g of polyvinylpyrrolidone (PVP) were sequentially added in a 1-L round-bottomed flask and mechanically stirred at room temperature. After bubbling with nitrogen for 15 minutes, the reaction system was heated to 75° C. under nitrogen protection and maintained for 30 minutes, and then 50 mL of an aqueous solution with 1 g of $K_2S_2O_8$ dissolved therein was slowly poured to the round-bottomed flask to initiate a polymerization reaction of styrene. The reaction was ended 24 hours later, a generated milky white reaction liquid was filtered and washed, and a collected filter cake was placed in a 60° C. vacuum oven for drying for 24 hours. A white filter cake after being dried was a three-dimensional template constructed by polystyrene microspheres, wherein the polystyrene microspheres had a size of about 270 nm.

Example 2

500 ml of deionized water, 65 ml of styrene and 2.5 g of polyvinylpyrrolidone (PVP) were sequentially added in a 1-L round-bottomed flask and mechanically stirred at room temperature. After bubbling with nitrogen for 15 minutes, the reaction system was heated to 80° C. under nitrogen protection and maintained for 30 minutes, and then 50 mL of an aqueous solution with 1 g of $K_2S_2O_8$ dissolved therein was slowly poured to the round-bottomed flask to initiate a polymerization reaction of styrene. The reaction was ended 24 hours later, a generated milky white reaction liquid was filtered and washed, and a collected filter cake was placed in a 60° C. vacuum oven for drying for 24 hours. A white filter cake after being dried was a three-dimensional template constructed by polystyrene microspheres, wherein the polystyrene microspheres had a size of about 240 nm.

Example 3

500 ml of deionized water, 65 ml of styrene and 2.5 g of polyvinylpyrrolidone (PVP) were sequentially added in a 1-L round-bottomed flask and mechanically stirred at room temperature. After bubbling with nitrogen for 15 minutes, the reaction system was heated to 85° C. under nitrogen protection and maintained for 30 minutes, and then 50 mL of an aqueous solution with 1 g of $K_2S_2O_8$ dissolved therein was slowly poured to the round-bottomed flask to initiate a polymerization reaction of styrene. The reaction was ended 24 hours later, a generated milky white reaction liquid was filtered and washed, and a collected filter cake was placed in a 60° C. vacuum oven for drying for 24 hours. A white filter cake after being dried was a three-dimensional template constructed by polystyrene microspheres, wherein the polystyrene microspheres had a size of about 210 nm.

Example 4

5 g of the three-dimensional template obtained in Example 1 was added to a methanol (45 mL) mixed solution containing 2-methylimidazole (13.5 g) and zinc nitrate hexahydrate (16.3 g), and stood still for 1 hour and then vacuum treated for 10 minutes. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water (25 wt %, the identification weight percentage hereinafter) and methanol with a volume ratio of the ammonia water to methanol being 1:1, vacuum treated for 3 minutes and then stood still for 24 hours, filtered, washed and then dried. After an obtained solid was added into tetrahydrofuran and soaked for 24 hours, the solid was repeatedly washed with tetrahydrofuran, and centrifugally separated to obtain MOF single crystals having an ordered macropore size of 270 nm.

Figure 2:
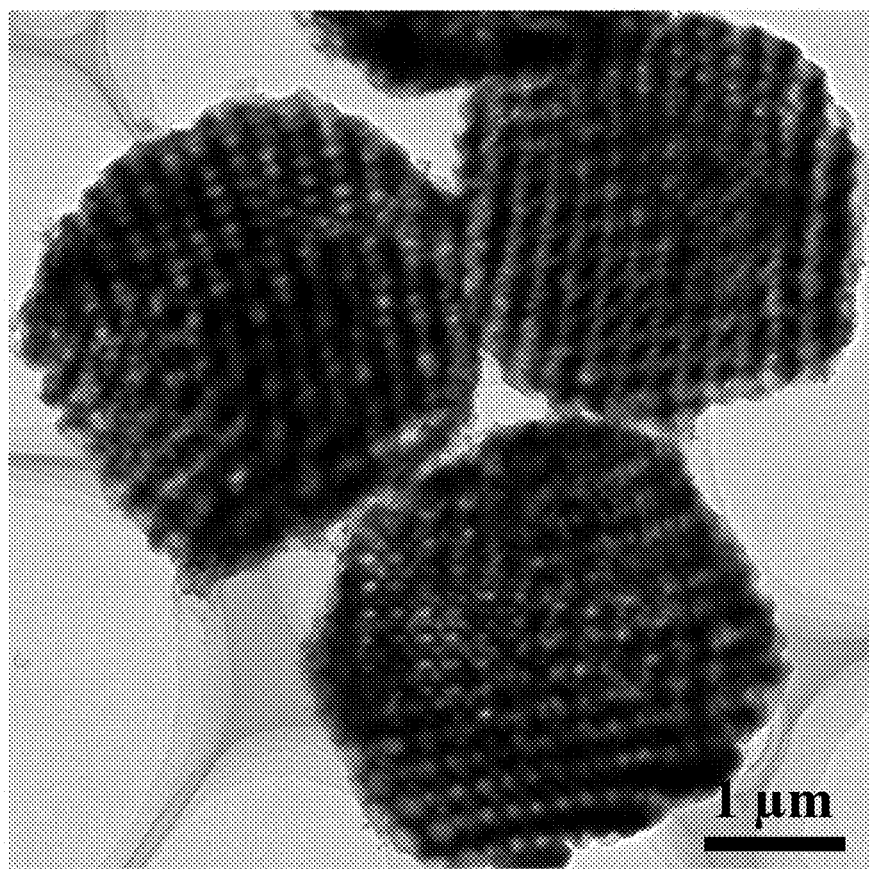
FIG. 2 is a transmission electron microscope image of the ordered macroporous MOF single crystals prepared in Example 4 of the present invention.
Figure 3:
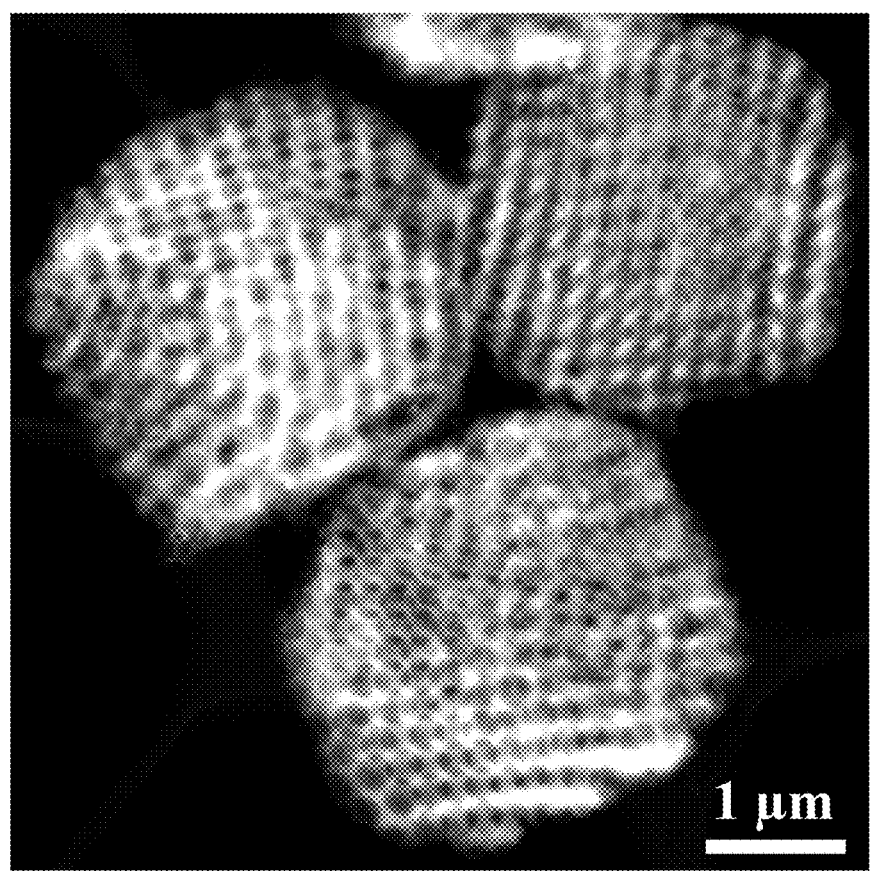
FIG. 3 is a scanning and transmission electron microscope image of the ordered macroporous MOFs single crystals prepared in Example 4 of the present invention.
Figure 4:
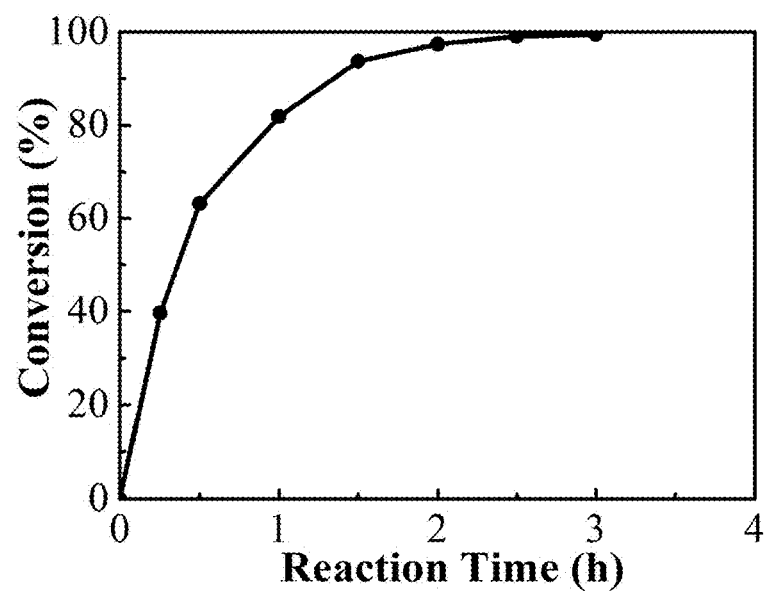
FIG. 4 is an evaluation graph of catalytic performance of the ordered macroporous MOF single crystals prepared in Example 4 of the present invention on a Knoevenagel reaction between benzaldehyde and ethanedinitrile.

FIG. 1 is a scanning electron microscope (SEM) image of ordered macroporous MOF single crystals prepared in this example. As seen from FIG. 1, the crystal has a size of about 2.3 μm, a large number of ordered macropores are arranged on the surface of the crystal. FIG. 2 is a transmission electron microscope (TEM) image of the ordered macroporous MOF single crystals prepared in this example. As seen from FIG. 2, it is clear that macro pores in the sample are distributed inside the entire crystal and these pores are highly ordered. FIG. 3 is a scanning transmission electron microscope (STEM) image of the ordered macroporous MOF single crystals. As seen from FIG. 3, an internal macroporous structure of the crystal may be clearly seen. FIG. 4 is an evaluation graph of catalytic performance of the sample on a Knoevenagel reaction between benzaldehyde and ethanedinitrile (reaction conditions: normal pressure and temperature, 6.6 mg of catalyst, 0.201 g of benzaldehyde, 0.251 g of ethanedinitrile, 5 mL of THF as a solvent, and mechanical stirring). As seen from FIG. 4, the catalyst may completely convert the benzaldehyde within a 2-hour reaction duration. The ordered macroporous MOF single crystals prepared in other examples have similar structures and catalytic performances as those of the ordered macroporous MOF single crystals in this example.

Example 5

Figure 5:
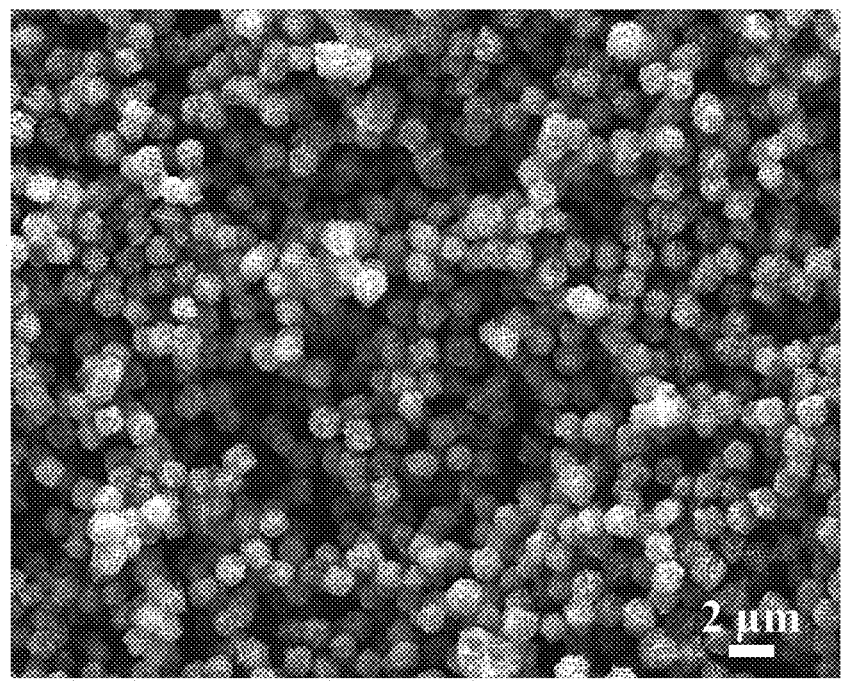
FIG. 5 is a scanning electron microscope image of ordered macroporous MOF single crystals prepared in Example 5 of the present invention.

5 g of the three-dimensional template obtained in Example 1 was added to a methanol (45 mL) mixed solution containing 2-methylimidazole (13.5 g) and zinc nitrate hexahydrate (16.3 g), and stood still for 1 hour and then vacuum treated for 10 minutes. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.33:0.67, vacuum treated for 3 minutes and then stood still for 24 hours, filtered, washed and then dried. After an obtained solid was added into tetrahydrofuran and soaked for 24 hours, the solid was repeatedly washed with tetrahydrofuran, and centrifugally separated to obtain a MOF single crystals having an ordered macropore size of 270 nm. FIG. 5 is a scanning electron microscope image of an ordered macroporous MOF single crystals prepared in this example. FIG. 5 is a scanning electron microscope image of ordered macroporous MOF single crystals prepared in this example.

Example 6

5 g of the three-dimensional template obtained in Example 1 was added to a methanol (45 mL) mixed solution containing 2-methylimidazole (13.5 g) and zinc nitrate hexahydrate (16.3 g), and stood still for 0 hour and then vacuum treated for 2 hours. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.2:0.8, vacuum treated for 3 minutes and then stood still for 24 hours, filtered, washed and then dried. After an obtained solid was added into tetrahydrofuran and soaked for 24 hours, the solid was repeatedly washed with tetrahydrofuran, and centrifugally separated to obtain MOF single crystals having an ordered macropore size of 270 nm.

Example 7

5 g of the three-dimensional template obtained in Example 1 was added to a methanol (45 mL) mixed solution containing 2-methylimidazole (13.5 g) and zinc nitrate hexahydrate (16.3 g), and stood still for 1 hour and then vacuum treated for 10 minutes. The three-dimensional template constructed by the polystyrene microspheres was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.8:0.2, vacuum treated for 2 hours and then stood still for 0 hour, filtered, washed and then dried. After an obtained solid was added into tetrahydrofuran and soaked for 24 hours, the solid was repeatedly washed with tetrahydrofuran, and centrifugally separated to obtain MOF single crystals having an ordered macropore size of 270 nm.

Example 8

5 g of the three-dimensional template obtained in Example 1 was added to a methanol (45 mL) mixed solution containing 2-methylimidazole (13.5 g) and zinc nitrate hexahydrate (16.3 g), and stood still for 12 hours and then vacuum treated for 10 minutes. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 1:0, vacuum treated for 1 hour and then stood still for 48 hours, filtered, washed and then dried. After an obtained solid was added into tetrahydrofuran and soaked for 24 hours, the solid was repeatedly washed with tetrahydrofuran, and centrifugally separated to obtain MOF single crystals having an ordered macropore size of 270 nm.

Example 9

5 g of the three-dimensional template obtained in Example 1 was added to a methanol (45 mL) mixed solution containing 2-methylimidazole (13.5 g) and zinc nitrate hexahydrate (8.15 g), and stood still for 1 hour and then vacuum treated for 0 minute. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.5:0.5, vacuum treated for 2 hours and then stood still for 24 hours, filtered, washed and then dried. After an obtained solid was added into tetrahydrofuran and soaked for 24 hours, the solid was repeatedly washed with tetrahydrofuran, and centrifugally separated to obtain MOF single crystals having an ordered macropore size of 270 nm.

Example 10

5 g of the three-dimensional template obtained in Example 1 was added to a methanol (45 mL) mixed solution containing 2-methylimidazole (6.75 g) and zinc nitrate hexahydrate (8.15 g), and stood still for 6 hours and then vacuum treated for 1 hour. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.5:0.5, vacuum treated for 0 minute and then stood still for 24 hours, filtered, washed and then dried. After an obtained solid was added into tetrahydrofuran and soaked for 24 hours, the solid was repeatedly washed with tetrahydrofuran, and centrifugally separated to obtain MOF single crystals having an ordered macropore size of 270 nm.

Example 11

5 g of the three-dimensional template obtained in Example 2 was added to a methanol (45 mL) mixed solution containing 2-methylimidazole (13.5 g) and zinc nitrate hexahydrate (16.3 g), and stood still for 1 hour and then vacuum treated for 10 minutes. The three-dimensional template constructed by the polystyrene microspheres was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.5:0.5, vacuum treated for 3 minutes and then stood still for 24 hours, filtered, washed and then dried. After an obtained solid was added into tetrahydrofuran and soaked for 48 hours, the solid was repeatedly washed with tetrahydrofuran, and centrifugally separated to obtain MOF single crystals having an ordered macropore size of 240 nm.

Example 12

5 g of the three-dimensional template obtained in Example 3 was added to a methanol (45 mL) mixed solution containing 2-methylimidazole (13.5 g) and zinc nitrate hexahydrate (16.3 g), and stood still for 1 hour and then vacuum treated for 10 minutes. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.5:0.5, vacuum treated for 3 minutes and then stood still for 24 hours, filtered, washed and then dried. After an obtained solid was added into tetrahydrofuran and soaked for 1 hour, the solid was repeatedly washed with tetrahydrofuran, and centrifugally separated to obtain MOF single crystals having an ordered macropore size of 210 nm.

Example 13

5 g of the three-dimensional template obtained in Example 1 was added to a methanol (45 mL) mixed solution containing 2-methylimidazole (2.3 g) and zinc nitrate hexahydrate (16.3 g), and stood still for 1 hour and then vacuum treated for 10 minutes. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.5:0.5, stood still for 24 hours, filtered, washed and then dried. After an obtained solid was added into tetrahydrofuran and soaked for 24 hour, the solid was repeatedly washed with tetrahydrofuran, and centrifugally separated to obtain MOF single crystals having an ordered macropore size of 270 nm.

Example 14

5 g of the three-dimensional template obtained in Example 1 was added to a methanol (45 mL) mixed solution containing 2-methylimidazole (22.5 g) and zinc nitrate hexahydrate (16.3 g), and stood still for 4 hours. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.5:0.5, stood still for 24 hours, filtered, washed and then dried. After an obtained solid was added into tetrahydrofuran and soaked for 24 hours, the solid was repeatedly washed with tetrahydrofuran, and centrifugally separated to obtain MOF single crystals having an ordered macropore size of 270 nm.

Example 15

5 g of the three-dimensional template obtained in Example 1 was added to a methanol (45 mL) mixed solution containing 2-methylimidazole (13.5 g) and zinc nitrate hexahydrate (4.1 g), and stood still for 1 hour and then vacuum treated for 10 minutes. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.5:0.5, vacuum treated for 3 minutes and then stood still for 24 hours, filtered, washed and then dried. After an obtained solid was added into tetrahydrofuran and soaked for 24 hours, the solid was repeatedly washed with tetrahydrofuran, and centrifugally separated to obtain MOF single crystals having an ordered macropore size of 270 nm.

Example 16

5 g of the three-dimensional template obtained in Example 1 was added to a methanol (25 mL) mixed solution containing 2-methylimidazole (22.5 g) and zinc nitrate hexahydrate (16.3 g), and stood still for 1 hour and then vacuum treated for 10 minutes. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.5:0.5, vacuum treated for 3 minutes and then stood still for 24 hours, filtered, washed and then dried. After an obtained solid was added into tetrahydrofuran and soaked for 24 hours, the solid was repeatedly washed with tetrahydrofuran, and centrifugally separated to obtain MOF single crystals having an ordered macropore size of 270 nm.

Example 17

5 g of the three-dimensional template obtained in Example 1 was added to a methanol (45 mL) mixed solution containing 2-methylimidazole (6.75 g) and zinc nitrate hexahydrate (8.15 g), and stood still for 1 hour and then vacuum treated for 10 minutes. The three-dimensional template was taken out from the solvent, and dried. Afterwards, the obtained three-dimensional template constructed by the polystyrene microspheres and containing 2-methylimidazole and zinc nitrate was soaked in a mixed solution of ammonia water and methanol with a volume ratio of the ammonia water to methanol being 0.5:0.5, vacuum treated for 3 minutes and then stood still for 24 hours, filtered, washed and then dried. After an obtained solid was added into tetrahydrofuran and soaked for 24 hours, the solid was repeatedly washed with tetrahydrofuran, and centrifugally separated to obtain MOF single crystals having an ordered macropore size of 270 nm.

The above examples are intended to illustrate and interpret the present invention instead of limiting the present invention. Within the sprit of the present invention and the protection scope defined by the appended claims, any modification or variation made to the present invention shall fall within the protection scope of the present invention.

What is claimed is:

1. A preparation method of ordered macroporous metal-organic framework single crystals, comprising the following steps:
   (1) dispersing polymer microspheres into a solvent, and preparing, through filtering or centrifugation, a three-dimensional template having periodic pore channels that is constructed by the polymer microspheres;
   (2) adding the three-dimensional template obtained in step (1) into a solution of 2-methylimidazole and zinc nitrate, standing still for 0 to 12 hours followed by vacuum treating for 0 to 2 hours, and then taking out the three-dimensional template and drying to obtain a microspherical three-dimensional template containing the 2-methylimidazole and the zinc nitrate;
   (3) adding the microspherical three-dimensional template containing the 2-methylimidazole and the zinc nitrate obtained in step (2) into a mixed solution of ammonia water and methanol, vacuum treating for 0 to 2 hours followed by standing still for 1 to 48 hours, and then filtering, washing and drying;
   (4) adding a solid obtained after drying in step (3) into an organic solvent for soaking, and then washing the solid and obtaining the macroporous metal-organic framework single crystals through centrifugal separation.

2. The preparation method according to claim 1, wherein the polymer microspheres in step (1) are uniformly sized polystyrene microspheres, polymethylmethacrylate microspheres, chitosan microspheres or polylactic acid microspheres.

3. The preparation method according to claim 1, wherein the solvent in step (1) is one or a mixture of methanol, ethanol, acetone, deionized water, dichloromethane and ethyl acetate.

4. The preparation method according to claim 1, wherein a molar ratio of the 2-methylimidazole to the zinc nitrate in step (2) is (0.5-5):1.

5. The preparation method according to claim 1, wherein a solvent of the solution in step (2) is one or a mixture of methanol, ethanol, acetone, deionized water, dichloromethane and ethyl acetate.

6. The preparation method according to claim 1, wherein a mass ratio of the 2-methylimidazole to the solvent in the solution in step (2) is 0.001 to 0.5 g/ml.

7. The preparation method according to claim 1, wherein a volume ratio of the methanol to the ammonia water in step (3) is (0-10):1.

8. The preparation method according to claim 1, wherein the organic solvent in step (4) is one or a mixture of N,N-dimethylformamide, toluene, tetrahydrofuran, dichloromethane and chloroform.

9. The preparation method according to claim 1, wherein the soaking in step (4) lasts for 1 to 48 hours.

10. An ordered macroporous metal-organic framework single crystals prepared by using the preparation method according to claim 1.

11. An ordered macroporous metal-organic framework single crystals prepared by using the preparation method according to claim 2.

12. An ordered macroporous metal-organic framework single crystals prepared by using the preparation method according to claim 3.

13. An ordered macroporous metal-organic framework single crystals prepared by using the preparation method according to claim 4.

14. An ordered macroporous metal-organic framework single crystals prepared by using the preparation method according to claim 5.

15. An ordered macroporous metal-organic framework single crystals prepared by using the preparation method according to claim 6.

16. An ordered macroporous metal-organic framework single crystals prepared by using the preparation method according to claim 7.

17. An ordered macroporous metal-organic framework single crystals prepared by using the preparation method according to claim 8.

18. An ordered macroporous metal-organic framework single crystals prepared by using the preparation method according to claim 9.

* * * * *